United States Patent [19]
Hong

[11] Patent Number: 6,017,303
[45] Date of Patent: Jan. 25, 2000

[54] UNDERPANTS WITH A STAMINA REINFORCING MECHANISM USING WALKING FORCE

[76] Inventor: Young-Soo Hong, 323 Yeonkun-dong, Jongro-ku, Seoul 110-460, Rep. of Korea

[21] Appl. No.: 08/714,106

[22] PCT Filed: Mar. 20, 1995

[86] PCT No.: PCT/KR95/00023

§ 371 Date: Sep. 23, 1996

§ 102(e) Date: Sep. 23, 1996

[87] PCT Pub. No.: WO95/26175

PCT Pub. Date: Oct. 5, 1995

[30] Foreign Application Priority Data

Mar. 25, 1994 [KR] Rep. of Korea .......................... 94/6078
Feb. 24, 1995 [KR] Rep. of Korea .......................... 95/3593

[51] Int. Cl.[7] ...................................................... A61F 5/00
[52] U.S. Cl. .............................. 600/38; 600/39; 128/842
[58] Field of Search .................................. 128/842, 844, 128/918; 604/347–353; 600/38–40; 602/67

[56] References Cited

U.S. PATENT DOCUMENTS

| 4,014,044 | 3/1977 | Figueroa | 602/67 |
| 4,852,586 | 8/1989 | Haines | 128/844 |
| 5,283,912 | 2/1994 | Chung. | |
| 5,472,399 | 12/1995 | Szekely | 600/38 |
| 5,535,758 | 7/1996 | Hagihara | 600/38 |

FOREIGN PATENT DOCUMENTS

| 647 399 | 1/1985 | Switzerland. |
| 2 256 144 | 12/1992 | United Kingdom. |

*Primary Examiner*—Michael A. Brown
*Attorney, Agent, or Firm*—Wenderoth, Lind & Ponack, L.L.P.

[57] ABSTRACT

An underpants with a stamina reinforcing mechanism using walking force, includes an underpants body provided with a waistband and leg insertion openings; supporting members respectively formed long perimeters of the leg insertion openings; and actuating members which move forward and backward in turn when the legs move forward and backward. One end of each actuating member is connected to the corresponding supporting member. A strengthening device rubs the glans of the penis by frictional contact as the actuating members move forward and backward in turn. The strengthening device is connected to the actuating member so that the strengthening device can surround the glans of the penis whereby the glans of the penis is naturally strengthened during walking.

13 Claims, 5 Drawing Sheets

UNDERPANTS WITH A STAMINA REINFORCING MECHANISM USING WALKING FORCE

BACKGROUND OF THE INVENTION

1. Field of the Invention

The present invention relates to underpants with a stamina reinforcing mechanism which operates using walking force. More particularly, the present invention relates to underpants with a stamina reinforcing mechanism using walking force by which the glans of the penis is rubbed against a plurality of projected pieces which are operated by the walking motions of the leg, such that stamina can be reinforced.

2. Description of the Prior Art

In these days, as the human desire for powerful stamina is gradually increased, various methods for reinforcing stamina are proposed in the art. A typical method for reinforcing stamina is taking a medicine or using a special mechanism. In the former case, the medicine has an essential limit in its effect and is apt to give rise to an adverse reaction. Also, in the latter case, since the mechanism works in the state in which the penis is fixedly held, it causes a counter result by degrading the stamina of a man from what he originally had.

Therefore, there has arisen a need for a stamina reinforcing mechanism which is capable of effectively increasing the stamina of a man without any adverse reaction or counter result. However, no prior art for such a mechanism has been found.

BRIEF DESCRIPTION OF THE DRAWINGS

The above object, and other features and advantages of the present invention will be more apparent after a reading of the following detailed description taken in conjunction with the drawings, in which.

SUMMARY OF THE INVENTION

Figure 1:
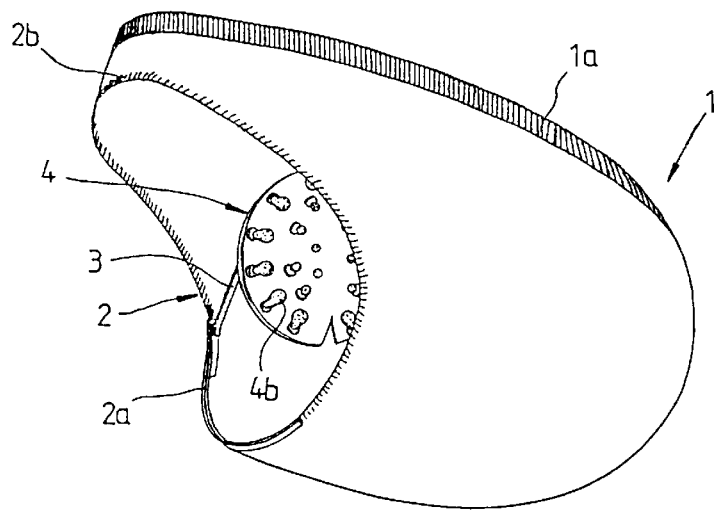
FIG. 1 is a perspective view of underpants with a stamina reinforcing mechanism using walking force in accordance with an embodiment of the present invention.
Figure 2:
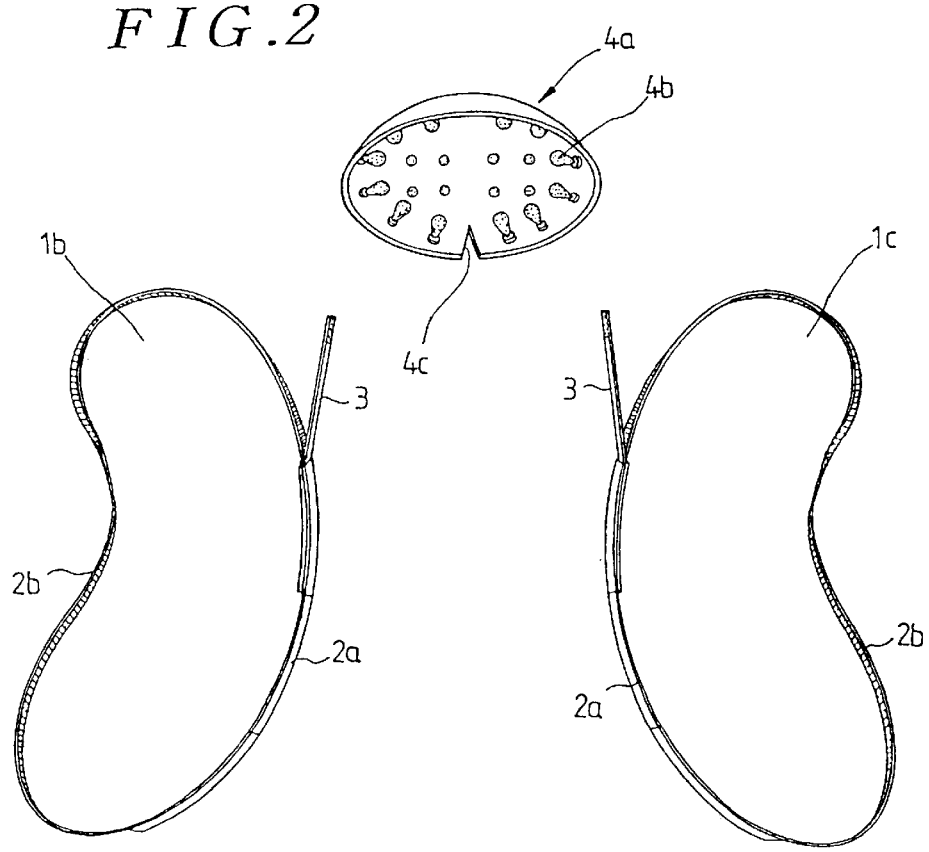
FIG. 2 is an exploded perspective view illustrating the stamina reinforcing mechanism shown in FIG. 1, independently.
Figure 3:
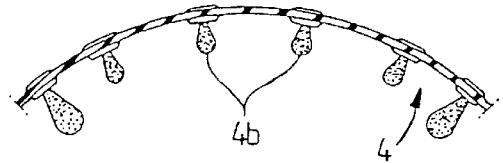
FIG. 3 is a partially enlarged cross-sectional plan view of a strengthening means used in the stamina reinforcing mechanism of FIG. 2.
Figure 4:
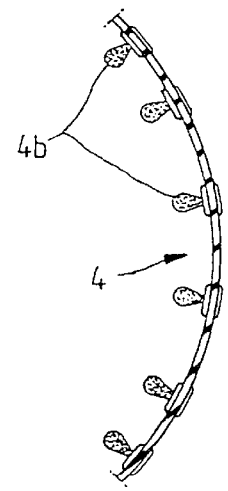
FIG. 4 is a partially enlarged longitudinal sectional view of a strengthening means used in the stamina reinforcing mechanism FIG. 2.

This above and other objects which will be apparent to one skilled in the art upon a reading of this disclosure are attained by:

An underpants with a stamina reinforcing mechanism using walking force comprising:

an underpants body provided with a waistband and two leg insertion openings;

two supporting means respectively formed along the perimeter of the leg insertion openings:

two actuating means which alternatively move forward and backward while both legs move forward and backward, one end of each actuating means being connected to the corresponding supporting means; and a strengthening means for rubbing the glans of the penis by frictional contact as the actuating means alternatively move forward and backward, the strengthening means being connected to the actuating means so that a strengthening means may surround the glans of the penis, whereby the glans of the penis is naturally strengthened during walking.

DETAILED DESCRIPTION OF THE PREFERRED EMBODIMENT

Referring now to FIGS. 1 to 5, there is illustrated underpants with a stamina reinforcing mechanism using walking force in accordance with one embodiment of the present invention. The underpants includes an underpants body 1. In the upper portion of the underpants body 1, there is provided a waistband 1a, and in the lower portion of the underpants body 1, there are defined two leg insertion openings 1b, 1c, respectively. Each of the leg insertion openings 1b, 1c has a supporting means 2 attached to the perimeter thereof. Each supporting means 2 includes a resilient band 2a, and a contractible band 2b which is connected to both ends of the resilient band 2a to obtain a ring-shaped appearance. The resilient band 2a is thin in thickness, narrow in width and contacts with the skin of the inside thigh portion of a man. The contractible band 2b can be made from rubber and contacts with the skin of the outside thigh portion of the man.

One end of each of the respective actuating means 3 is connected to one resilient band 2a of the supporting means 2. An actuating means 3 is also thin in thickness, narrow in width and can be made from resilient material. The actuating means 3 is alternately moved forward and rearward in line with the walking motion of the legs to transfer power. The other end of each of the actuating means 3 is connected to a strengthening means 4 which surrounds the glans of the penis.

In order to maximize the power produced from both legs which are alternately moved forward and rearward upon walking, the resilient bands 2a of the supporting means 2 are disposed in the leg insertion openings 1b, 1c respectively, to contact with the inside rearward portion of the thigh of the man, and the one end of each of the actuating means 3 is connected to a forward end of one of the resilient bands 2a.

Each of the actuating means 3 can be integrally formed with the resilient band 2a of the supporting means 2, or can be detachably connected to the resilient band 2a of the supporting means 2 by a detachable means so as to be detached when desired. A magic tape or a snap can be used as the detachable means, in a non restricting manner.

The strengthening means 4 includes a strengthening plate 4a which is connected to both of the other ends of the supporting means 3 to surround the glans of the penis, and a plurality of projected pieces 4b which are attached to the inner surface of the strengthening plate 4a to be resiliently flexed upon contacting with the glans of the penis to excite it. The strengthening plate 4a is made of flexible material, for example soft cloth. A cut-out portion 4c is formed in the lower center part of the strengthening plate 4a to effectively surround the glans. The strengthening plate 4a can be integrally formed with the actuating means 3, or can be detachably connected to the actuating means 3 using another detachable means.

Figure 5:
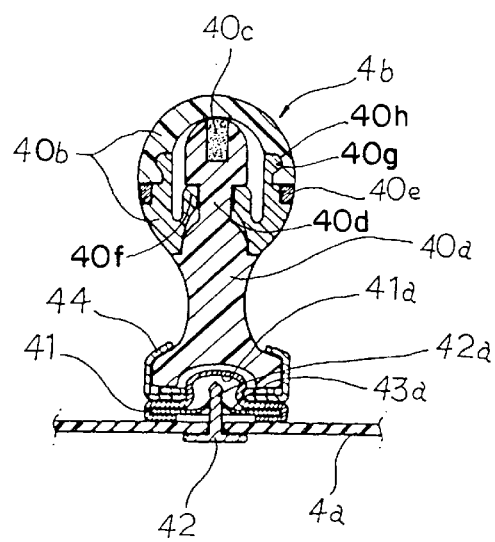
FIG. 5 is an enlarged cross-sectional view illustrating the structure of one of a plurality of projected pieces attached to the strengthening means of FIGS. 3 and 4.
Figure 6:
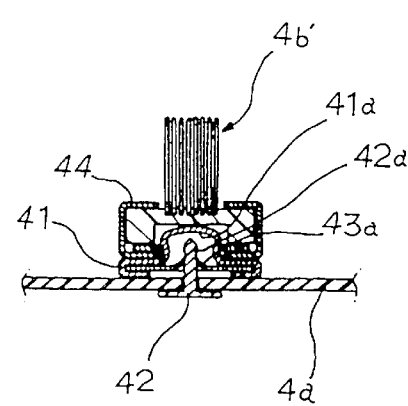
FIG. 6 is an enlarged cross-sectional view of a projected piece in accordance with another embodiment of the present invention.

The projected pieces 4b are attached to the strengthening plate 4a in a snap-fitted manner, and the free end of each projected piece 4b is directed to the glans of the penis. Each projected piece 4b has a mushroom or bowling pin shaped inner body 40a and an outer body 40b. Inner body 40a is made from resilient material such as rubber to be elastically moved upon contacting with the glans of the penis. Outer body 40b is made from a material such as silicon rubber, ceramic, and it covers the outer surface of inner body 40a, and is to make frictional contact with the glans of the penis during walking. The elasticity of the projected piece 4b serves to increase the stamina reinforcing effect of the present invention. Also, as best seen in FIG. 5, a magnet 40c is embedded in the projected piece 4b to enhance the stamina reinforcing effect using a magnetic force change. In the projected piece 4b constructed as described above, inner body 40a and outer body 40b are separately formed, and assembled after stainless plates 40d, 40e are fitted to the outer part of inner body 40a and the inner part of outer body 40b, respectively. The free end of the inner body 40a is formed with a groove 40f into which the magnet 40c is seated. Instead of the magnet 40c, the perfume may be provided in groove 40f when desired. A magnetic force passing opening 40g is formed in stainless plate 40e to ensure the free passage of the magnetic force. When perfume is provided in groove 40f of the inner body 40a, a hole is formed in the outer body 40b to ensure release of the perfume. In the strengthening means 4b is not restricted to that shown, but rather various projected piece structures can be used according to desired effect and taste. For example, as shown in FIG. 6, projected piece 4b' made of soft brushes can be used.

A stamina reinforcing method for use with the underpants in accordance with this embodiment of the present invention will be described below with reference to FIGS. 7 to 9.

Figure 7:
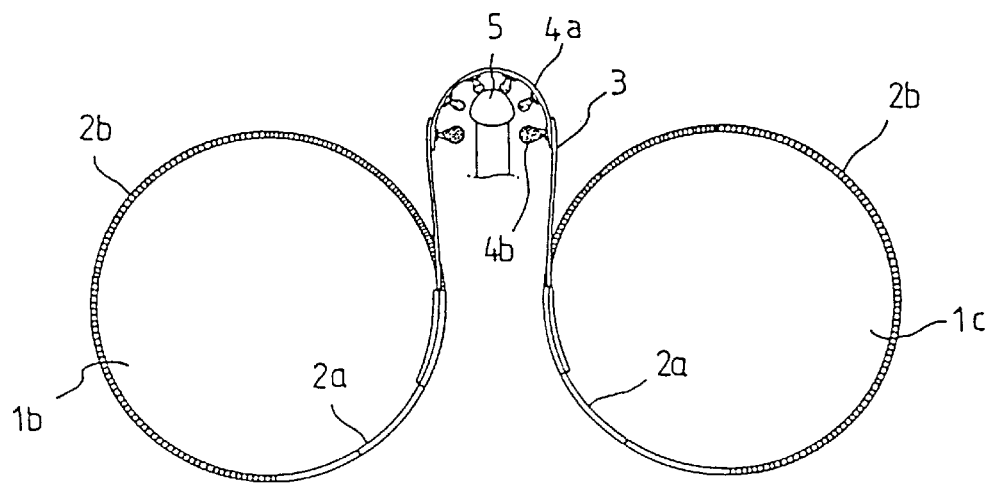
FIGS. 7 to 9 are views illustrating the operating procedure of the underpants with a stamina reinforcing mechanism using walking force in accordance with the present invention.

Referring now to FIG. 7, there is illustrated an initial stage in which the underpants of the present invention are worn and the legs of the man are maintained in a straight line. The strengthening plate 4a is positioned so as to surround the glans of the penis 5, and both actuating means 3 are maintained in a side by side relationship.

Figure 8:
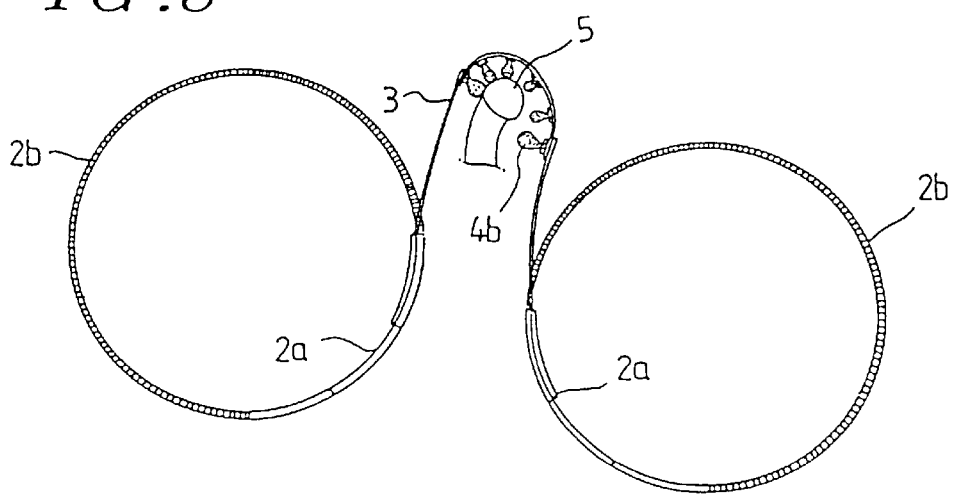
Figure 9:
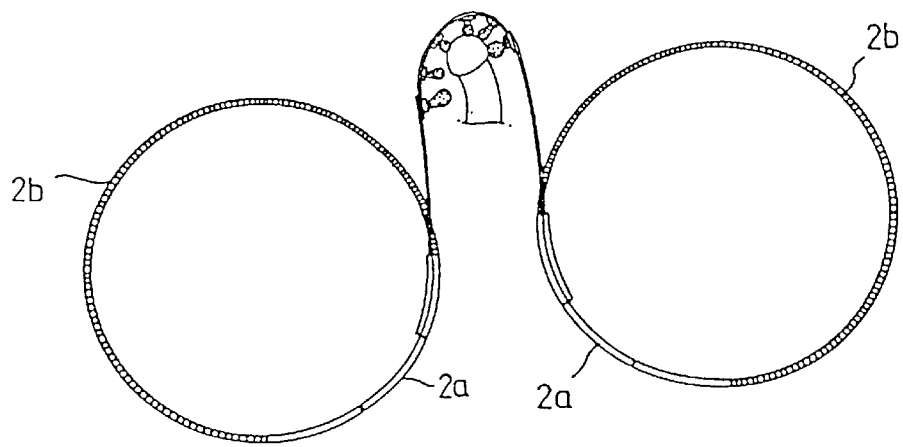

From this stage, when one of the legs moves forward, the front end of an actuating means 3 connected to a resilient band 2a surrounding the forwardly-moved thigh approaches the glans of the penis; the front end of an actuating means 3 connected to a resilient band 2a surrounding the other thigh recedes from the glans of the penis, as shown in FIGS. 8 and 9. To explain such action in detail, when one of the actuating means 3 positioned on right and left sides of the penis moves forward, the other of them is pulled backward. Such action is alternately repeated according to the movement of the legs. In this embodiment, a plurality of projected pieces 4b of a strengthening plate 4a rub the glans of the penis by frictional contact during walking since they surround the glans of the penis.

As described above in detail, the underpants with a stamina reinforcing mechanism using walking force operate to strengthen the glans of the penis by rubbing it by frictional contact during walking. Therefore, it will be appreciated that the present invention, as described above, achieves naturally a stamina reinforcing effect during walking. In addition, the underpants according to the present invention are very convenient to wear since they have only a stamina reinforcing mechanism attached to ordinary underpants. Moreover, providing a plurality of resilient projected pieces and magnets located inside them enhances stamina effectively since these projected pieces rub the surface of the glans of the penis with the magnets in motion during walking.

Figure 10:
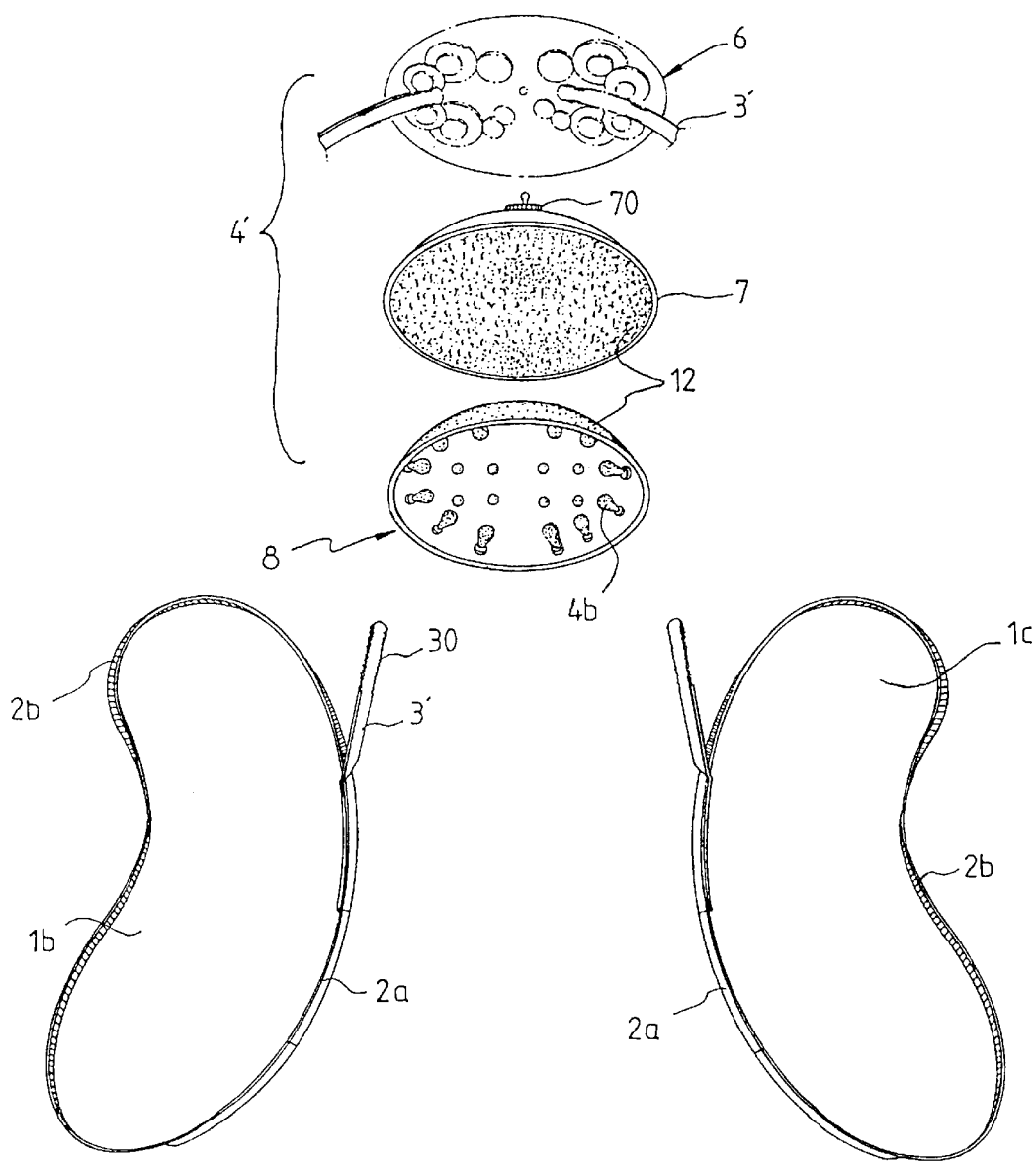
FIG. 10 is an exploded perspective view illustrating a stamina reinforcing mechanism in accordance with another embodiment of the present invention, independently.

As illustrated in FIG. 10, which illustrates another embodiment of a stamina reinforcing mechanism, this embodiment is characterized in that the stamina may be strengthened not by pushing forward and pulling backward the strengthening plate but by alternatively rotating the strengthening plate in opposite directions. In an alternate embodiment of FIG. 10, the stamina reinforcing means 4' is comprised of a power transference and conversion means 6; a rotating member 7 connected to a power transference and conversion means 6; and a hollow hemispherical strengthening plate 8 having a plurality of projected pieces 4b on its inner surface and a magic tape 12 on its outer surface. The power transference and conversion means 6 has the function of receiving the straight line motion from actuating means 3' and rotating the rotating member 7 connected to the power transference and conversion means 6. The rotating member 7 is of a hollow hemispherical shape and has a magic tape 12 on its inner face.

A center gear 70 is formed at the center of the outer face of the rotating member 7. Rack gears 30 respectively are formed at the ends of the actuating means 3' in order to convert a straight line motion to a rotating motion.

Therefore, the straight line motion of the actuating means 3' during walking is converted to the rotating motion by a power transference and conversion means 6. The rotating member 7 is rotated since the rotating motion is transferred to the center gear 70 fixedly attached to the rotating member 7. Accordingly, the strengthening plate 8 connected to the rotating member 7 rotates and a plurality of projected pieces attached thereto rub the glans of the penis by frictional contact as the rotating member 7 rotates.

Figure 11:
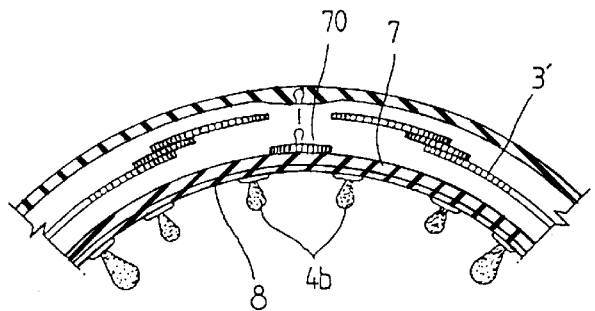
FIG. 11 is a partially enlarged cross-sectional plan view of a projected means used in the stamina reinforcing mechanism of FIG. 10.
Figure 12:
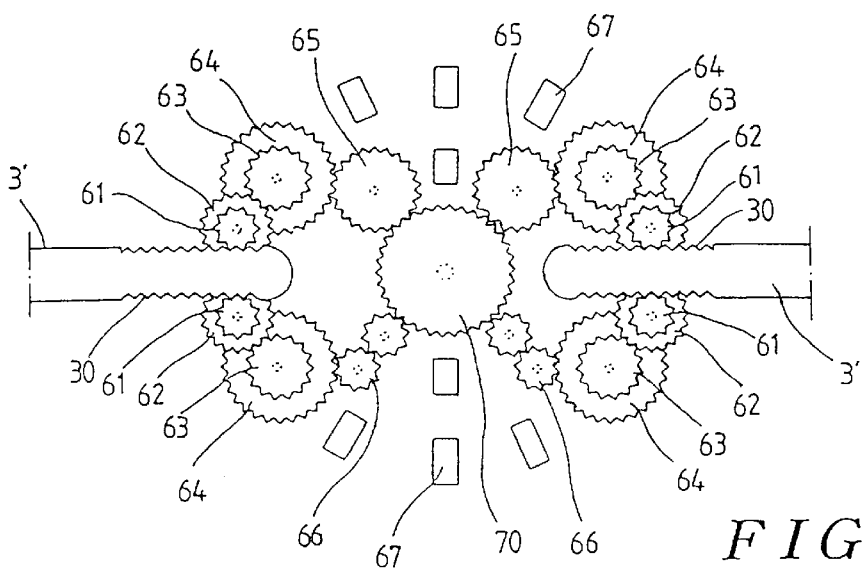
FIG. 12 is a front view illustrating the power transfer structure of a gear train included in the strengthening means of FIG. 11.

In FIG. 11, the construction of the strengthening means is shown in a partial enlarged view. In FIG. 12, the process of transferring power of a power transference and conversion means 6 is shown in detail.

In FIGS. 11 and 12, the straight line motions of rack gears 30 are respectively converted to the rotating motion by the pinions 61, an then the rotating motion is transferred to the center gear 70 by way of the intermediate gears 62, 63, 64 and 65. Therefore, the rotating member 7 rotates. The movement of both actuating means 3' according to walking makes the center gear 70 rotate alternately in clockwise and counter clockwise directions. That is to say, when one actuating means moves forward, the other actuating means moves backward. Such movement is repetitive during walking. Gears 66 function to harmonize the overall rotating direction. Rollers 67 make the strengthening plate 8 rotate smoothly. The other elements comprising the strengthening means, for example a plurality of projected pieces, are not described here since those are the same as in the first embodiment.

Figure 13:
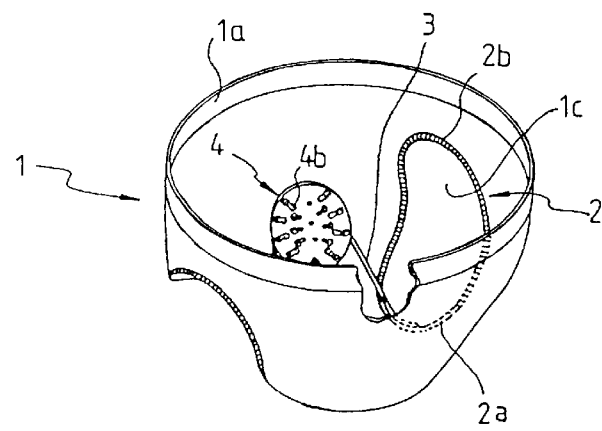
FIG. 13 is a perspective view illustrating the state in which a stamina reinforcing device in accordance with still another embodiment is put into conventional underpants.

FIG. 13 illustrates still another embodiment of the present invention in which the stamina reinforcing device using walking force is formed separately from the underpants.

In FIG. 13, the stamina reinforcing device using walking force comprises two supporting means 2 worn on both thighs; two actuating means 3 connected thereto for moving forward and backward alternately according to the movement of both legs during walking; and a strengthening means 4 connected to the actuating means 3 for rubbing the glans of the penis according to the forward and backward movement of the actuating means 3. The detailed construction of stamina reinforcing device using walking force is the same as in the first and second examples described above. This stamina reinforcing device, as shown in FIG. 13, may also be attached to the underpants.

The strengthening action and the effect thereof by rubbing the surface of the glans of the penis in this embodiment are the same as in the first and second embodiments except that the stamina reinforcing device may be detached from the ordinary underpants as desired.

In addition, the stamina strengthening method according to the present invention is as follows:

Both thighs respectively approach and recede from the glans of the penis while both legs respectively alternately move forward and backward since the penis of the man is placed in front of the human body between both thighs. The power for operating the device originates from the movement of the thighs during walking. This power is applied to the rubbing of the glans of the penis by frictional contact and hence the glans of the penis is strengthened during walking.

According to the present invention, the stamina increases naturally during the daily life since the walking force is used as a power source without using special power.

Having described the preferred embodiments of the present invention, it will appear to those of ordinary skill in the art that various modifications may be made to the disclosed embodiments, and that such modifications are intended to be within the scope of the present invention.

I claim:

1. An underpants with a stamina reinforcing mechanism using walking force, comprising:

an underpants body provided with a waistband and a pair of leg insertion openings for receiving legs, respectively, of a man;

a pair of supporting members respectively formed along perimeters of said leg insertion openings;

a pair of actuating members having first ends connected to said supporting members, respectively, so as to alternately move forward and backward while the legs move forward and backward; and a strengthening device connected to said actuating members so as to surround a glans of the penis of the man and rub the glans of the penis as said actuating members move forward and backward, whereby the glans of the penis is naturally strengthened during walking.

2. An underpants as in claim 1, wherein said strengthening device comprises a concave strengthening plate.

3. An underpants as in claim 1, wherein each of said supporting members comprises a resilient band for contacting an inside portion of a thigh of the man and a flexible band contacting an outside portion of the thigh, wherein each of said bands forms a ring, and each of said actuating members is connected to one of said flexible bands.

4. An underpants as in claim 1, wherein each of said actuating members has a thin and narrow band shape and is detachably connected to one of said supporting members.

5. An underpants as in claim 1, wherein said strengthening device comprises a round strengthening plate connected to a second end of each of said actuating members so that said strengthening device can surround the glans of the penis, and a plurality of projected pieces attached to an inner face of said strengthening plate so that said projected pieces can swing around the glans of the penis and stimulate the glans of the penis.

6. An underpants as in claim 5, wherein said projected pieces are formed so that they can shake resiliently and are detachably attached, and each of said projected pieces has a magnet or perfume at an inside thereof, and wherein an outer shell of each of said projected pieces is made of silicon rubber or ceramic material with an irregular surface and holes.

7. An underpants as in claim 1, wherein each of said projected pieces is connected to said strengthening plate by a snap arrangement comprising a male snap portion provided on one of said projected piece and said strengthening plate, and a female snap portion, engageable with said male snap portion, provided on the other of said projected piece and said strengthening plate.

8. An underpants as in claim 1, wherein said strengthening device comprises a concave strengthening plate, a plurality of projected pieces on an inner surface of said strengthening plate, a rotating member connected to said strengthening plate, a center gear provided on said rotating member, and a power transference and conversion device operably connected to said actuating members and said center gear to rotate said center gear upon forward and backward movement of said actuating members during walking.

9. An underpants as in claim 8, wherein said power transference and conversion device comprises rack gears operably coupled to said center gear and to said actuating members.

10. An underpants as in claim 1, wherein said strengthening device comprises a concave strengthening plate, a plurality of projected pieces on an inner surface of said strengthening plate, and a rotary mechanism connected to said actuating members for rotating said strengthening plate as the legs move forward and backward during walking.

11. A stamina reinforcing device using walking force of a man, comprising:

a pair of supporting members worn on thighs of the man, respectively;

a pair of actuating members connected to said supporting members, respectively, for alternately moving forward and backward according to movement of legs of the man during walking; and a strengthening device connected to said actuating members and surrounding a glans of the penis of the man for rubbing the glans of the penis by frictional contact according to the forward and backward movement of said actuating members, respectively.

12. A method of reinforcing stamina of a man's penis by rubbing a glans of the penis by frictional contact by utilizing a power derived from movement of thighs of the man respectively moving toward and away from the glans of the penis while legs of the man respectively move forward and backward in turn during walking whereby the glans of the penis is strengthened during walking.

13. An underpants comprising:

an underpants body;

a plate attached at a front inner portion of said underpants body;

a plurality of resilient strengthening balls projected from said plate inwardly of said underpants body so as to contact with a glans of the penis of a man when the man wears the underpants, whereby the glans of the penis is naturally strengthened by wearing the underpants.

* * * * *